United States Patent
Oura et al.

(10) Patent No.: US 9,291,572 B2
(45) Date of Patent: Mar. 22, 2016

(54) METHOD AND APPARATUS FOR MEASURING PH OF MEDIUM SOLUTION

(75) Inventors: Mitsuhiro Oura, Tokyo (JP); Hirotsugu Kubo, Tokyo (JP); Sunao Takeda, Tokyo (JP); Teruo Okano, Tokyo (JP); Tatsuya Shimizu, Tokyo (JP)

(73) Assignees: NIHON KOHDEN CORPORATION, Tokyo (JP); TOKYO WOMEN'S MEDICAL UNIVERSITY, Tokyo (JP)

(*) Notice: Subject to any disclaimer, the term of this patent is extended or adjusted under 35 U.S.C. 154(b) by 921 days.

(21) Appl. No.: 13/441,630

(22) Filed: Apr. 6, 2012

(65) Prior Publication Data

US 2012/0253692 A1 Oct. 4, 2012

(30) Foreign Application Priority Data

Mar. 31, 2011 (JP) ................................. 2011-079705

(51) Int. Cl.
*G01N 21/31* (2006.01)
*G06F 19/00* (2011.01)
(Continued)

(52) U.S. Cl.
CPC ............... *G01N 21/80* (2013.01); *C12M 41/26* (2013.01); *G01N 31/221* (2013.01); *G01N 2021/3148* (2013.01); *G01N 2021/3181* (2013.01); *G01N 2201/0627* (2013.01)

(58) Field of Classification Search
CPC ..... G01N 21/274; G01N 33/52; G01N 33/66; G01N 21/08; G01N 31/221; G01N 2021/3148; G01N 2021/3181; G01N 2201/0627; Y10T 436/142222; Y10T 436/112499; Y10T 436/144444; Y10T 436/143333; C12M 41/26

USPC ......... 436/95, 46, 93, 94, 163, 164, 166, 169, 436/172; 422/56, 82.08, 82.09, 412; 702/30; 356/412
See application file for complete search history.

(56) References Cited

U.S. PATENT DOCUMENTS 6,121,050 A * 9/2000 Han ..................... G01N 21/274
  422/412
6,379,969 B1 * 4/2002 Mauze ............... G01N 21/6428
  422/82.05

(Continued)

FOREIGN PATENT DOCUMENTS

GB   2412171 A    9/2005
JP   6-34754 B2   5/1987
(Continued)

OTHER PUBLICATIONS

Search Report for European Patent App. No. 12162312.8 dated Apr. 23, 2013.

(Continued)

*Primary Examiner* — Alexander H Taningco
*Assistant Examiner* — Seokjin Kim
(74) *Attorney, Agent, or Firm* — Kenealy Vaidya LLP

(57) ABSTRACT

A pH measuring method includes: illuminating a medium solution, which includes: a first material; and a second material, with a plurality of light beams, which includes: a first light beam, a wavelength of which corresponds to a first absorption peak; a second light beam, a wavelength of which corresponds to a second absorption peak or a second convergence point; a third light beam, a wavelength of which corresponds to a third absorption peak or a third convergence point; and a fourth light beam, a wavelength of the fourth light beam at which an absorbance of at least one of the first and second materials is converged irrespective of a pH; receiving transmitted or reflected light beams of the first to fourth light beams; measuring absorbances at the wavelengths of the received light beams respectively; and calculating a pH of the medium solution based on the absorbances.

11 Claims, 17 Drawing Sheets

(51) Int. Cl.
*G01N 21/80* (2006.01)
*G01N 31/22* (2006.01)
*C12M 1/34* (2006.01)

(56) References Cited

U.S. PATENT DOCUMENTS

| | | | |
|---|---|---|---|
| 6,913,930 B2* | 7/2005 | Bevan et al. | 436/163 |
| 7,961,327 B1* | 6/2011 | LoPresti | G01N 21/55 |
| | | | 250/227.21 |
| 2004/0009606 A1* | 1/2004 | Kimball | A61B 5/14539 |
| | | | 436/163 |
| 2008/0188722 A1* | 8/2008 | Markle | G01N 33/66 |
| | | | 600/316 |
| 2008/0311614 A1* | 12/2008 | Lee | 435/29 |
| 2008/0318307 A1 | 12/2008 | Spittle et al. | |
| 2010/0240141 A1* | 9/2010 | Nakano | 436/163 |
| 2012/0214250 A1* | 8/2012 | Oura | G01N 21/80 |
| | | | 436/163 |

FOREIGN PATENT DOCUMENTS

| | | |
|---|---|---|
| JP | 1-165938 A | 6/1989 |
| JP | 2-85745 A | 3/1990 |
| JP | 2009-198488 A | 9/2009 |
| WO | 2009/093401 A1 | 7/2009 |

OTHER PUBLICATIONS

Japanese Office Action for the related Japanese Patent Application No. 2011-079705 dated Oct. 28, 2014.

* cited by examiner

ND APPARATUS FOR
MEASURING pH OF MEDIUM SOLUTION

BACKGROUND OF THE INVENTION

The present invention relates to a method of measuring the pH of a cell culture solution, and also to an accurate pH measuring method and apparatus in which an influence of a predetermined component such as a cell proliferation factor of fetal bovine serum (FBS) that is contained in a medium and that has an unknown concentration is corrected.

In order to grow and proliferate cells, the pH of a culture solution containing the cells must be within a range suitable for proliferation. During preparation or storage of such a cell culture solution, however, carbon dioxide which is contained in the cell culture solution is released, and the pH is increased, so that the pH is often deviated from the proliferation suitable range.

Therefore, the pH is measured by a method in which, for example, the color change of phenol red that is contained in a cell culture solution is visually checked, or that in which the measurement is performed while pH electrodes are immersed in a cell culture solution. However, these methods have the following problems.

In the case where the color change of phenol red contained in a cell culture solution is visually checked, an erroneous check may be caused. This is because an error often occurs in a visual check, and serum contained in a cell culture solution, such as fetal bovine serum exhibits a yellow color, and hence a check result is sometimes confused by the coloration.

By contrast, in the case where pH electrodes are immersed in a cell culture solution, when the pH electrodes are not sufficiently sterilized, contamination due to bacteria or the like may occur.

As a method of measuring the pH of a cell culture solution which is free from problems such as an error due to a visual check, and contamination in the case where pH electrodes are used, the following method is known (see JP-B-06-34754).

FIG. 1 is a block diagram showing a pH measuring apparatus which can measure the pH of a medium solution.

In the pH measuring apparatus of the example, a light emitting element 1 is driven by a driving circuit 3 so as to emit light beams by using an electric power supplied from a battery 4.

Although the light emitting element 1 is shown as one element in FIG. 1, the light emitting element is actually configured by a plurality of elements respectively emitting light beams of different wavelengths. More specifically, the light emitting element 1 is configured by at least four elements such as: an element emitting a light beam of 411 nm band which is a peak of the absorbance corresponding to fetal bovine serum (FBS); that emitting a light beam of 430 or 560 nm band indicating a peak of the absorbance of phenol red (pH indicator); that emitting a light beam of 367 or 479 nm band indicating a value to which the absorbance is unchanged and converged irrespective of a change of the pH; and that emitting a light beam of 700 nm band in which, for example, fetal bovine serum and phenol red do not exhibit absorbance. For example, LEDs are preferably used as these elements.

The light beams emitted from the light emitting element 1 are transmitted through a solution 5 in which the pH is to be measured, and then received by a light receiving element 6, to be converted to electric signals. Although the light receiving element 6 is shown as one element in FIG. 1, the light receiving element is actually configured by a plurality of elements respectively corresponding to the elements constituting the light emitting element 1. Photodiodes are preferably used as these elements. In the case where the light emitting element 1 is configured by four LEDs, namely, the light receiving element 6 may be configured by four photodiodes. In place of the mode where the light receiving element 6 receives light beams which have been transmitted through the measurement solution 5, the light receiving element may be disposed so as to receive light beams reflected from the measurement solution 5.

The signals which are converted in the light receiving element 6 are amplified by an amplifier 7, and then distributed by a multiplexer 8 to filters 9 which correspond to the light wavelengths, respectively.

The signals distributed to the filters 9 are filtered by the filters 9 to reduce noise components, digitized by an A/D converter which is not shown, and then supplied to a processing section 10. For example, the processing section 10 is configured by a calculation processing device such as a CPU, a storage device, etc.

JP-B-06-34754 describes a related-art method of measuring the pH of a cell culture solution as follows.

The method of measuring the pH of a cell culture solution is a method in which the pH is measured based on absorption of visible light in a cell culture solution configured by: a cell culture medium; serum; and an indicator having two or more kinds of absorption peaks in the wavelength region of visible light, wherein, based on a linear relationship between the pH and the logarithms of absorbances at two wavelengths of absorption peaks that are obtained by transmitting visible light through a cell culture solution in which the pH is known, the value of the pH is obtained from the value of the logarithm of a ratio of absorbances of absorption peaks that are measured in a cell culture solution specimen in which the pH is not known.

In the cell culture solution, usually, phenol red for detecting a change of the pH is contained at a low concentration which does not harm cells. In the visible light range, at such a low concentration, phenol red has peaks in the vicinities of 430 to 440 nm and 560 nm, and an isosbestic point at 480 nm. In a pH range of 6.8 to 7.6 where cells can grow, as the pH is further lowered, the absorption peak in the vicinity of 430 to 444 nm is more increased, and that in the vicinity of 560 nm is more decreased. When absorption due to only the phenol red is obtained, by taking a ratio of absorption in the vicinity of 430 to 440 nm to that in the vicinity of 560 nm, the plot shows one curve, and the pH of the culture solution can be calculated from a ratio of the two peaks.

In the related-art optical pH measurement, moreover, the zero level measurement is performed with a sample blank prior to measuring the sample, and the absorption levels of the blank are then subtracted from the sample reading to provide the net absorbance of the sample. The vicinity of the wavelength (700 nm) which shows very little absorption by the indicator is chosen as the third wavelength, and is used as means for tracking changes in the zero level. Changes in the absorption level of this wavelength channel are indicative of changes in the zero level. Therefore, the other two wavelengths which are used in the measurement are zero corrected based on the changes measured at this third wavelength.

In the related-art method of measuring the pH of a cell culture solution disclosed in JP-B-06-34754, only phenol red is contained in the cell culture solution. In a cell culture solution, however, not only phenol red, but also, for example, fetal bovine serum (FBS) is sometimes contained as a proliferation factor for proliferating cells.

The optical absorbance characteristic of fetal bovine serum (FBS) is largely different from that of phenol red, and hence a measurement value obtained in the pH measuring method disclosed in JP-B-06-34754 cannot be used as it is. In the pH measuring method disclosed in JP-B-06-34754, particularly, a linear relationship between the logarithms of absorbances and the pH cannot be determined unless the concentration of the serum contained in the medium is known before the measurement. In a medium containing, for example, serum the concentration of which is unknown, therefore, the pH cannot be correctly measured.

SUMMARY

It is therefore an object of the invention to provide a pH measuring method in which the pH of a cell culture solution can be correctly measured irrespective of the concentration of a proliferation factor such as fetal bovine serum (FBS) contained in the cell culture solution, and also an apparatus for measuring pH of a cell culture solution.

In order to achieve the object, according to the invention, there is provided a pH measuring method comprising: illuminating a medium solution with a plurality of light beams, the medium solution including: a first material which, in a wavelength region of 300 nm to 800 nm, has a first absorption peak; and a second material which, in the wavelength region of 300 nm to 800 nm, has a second absorption peak or a second convergence point where an absorbance is converged irrespective of a pH, and a third absorption peak or a third convergence point where an absorbance is converged irrespective of a pH, the plurality of light beams including: a first light beam, a wavelength of which corresponds to the first absorption peak; a second light beam, a wavelength of which corresponds to the second absorption peak or the second convergence point; a third light beam, a wavelength of which corresponds to the third absorption peak or the third convergence point; and a fourth light beam, a wavelength of the fourth light beam at which an absorbance of at least one of the first material and the second material is converged irrespective of a pH; receiving transmitted or reflected light beams of the first to fourth light beams; measuring absorbances at the wavelengths of the received transmitted or reflected light beams of the first to fourth light beams respectively; and calculating a pH of the medium solution based on the measured absorbances.

The pH of the medium solution may be calculated with correction using multiple regression analysis in which a logarithm of an absorbance ratio calculated from the measured absorbances is employed.

The multiple regression analysis may be performed by a regression expression indicated by following expression:

$$pH = B_0 + B_1 * \Phi_{\lambda i/\lambda j}$$

$$\Phi_{\lambda i/\lambda j} = \log(A_{\lambda i}/A_{\lambda j})$$

$$pH = B_0 + B_1 * \Phi_{\lambda 1/\lambda 4} + B_2 * \Phi_{\lambda 2/\lambda 4} + B_1 * \Phi_{\lambda 3/\lambda 4}.$$

The pH of the medium solution may be calculated with an expression including a sum of the absorbance of the first material and the absorbance of the second material.

The expression may include one of a first function in which the pH is a variable and a second function in which an absorption coefficient is a variable.

In a case where the expression includes the first function, the pH may be calculated by following expression:

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ pH \cdot C_{PR} \cdot D \\ C_{PR} \cdot D \\ A_{offset} \end{pmatrix}$$

where $$\begin{pmatrix} A_{\lambda 1} \\ A_{\lambda 2} \\ A_{\lambda 3} \\ A_{\lambda 4} \end{pmatrix}$$

is measurable, $$\begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}$$

is known, and $$\begin{pmatrix} C_{FBS} \cdot D \\ pH \cdot C_{PR} \cdot D \\ C_{PR} \cdot D \\ A_{offset} \end{pmatrix}$$

is unknown.

In a case where the expression includes the second function, the pH may be calculated based on an absorption coefficient which is obtained by following expression:

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ \alpha_{PR\_\lambda 1} \cdot C_{PR} \cdot D \\ C_{PR} \cdot D \\ A_{offset} \end{pmatrix}$$

where $$\begin{pmatrix} A_{\lambda 1} \\ A_{\lambda 2} \\ A_{\lambda 3} \\ A_{\lambda 4} \end{pmatrix}$$

is measurable, $$\begin{pmatrix} \alpha_{FBS\_\lambda1} & 1 & 0 & S_{\lambda1} \\ \alpha_{FBS\_\lambda2} & B_{0\_\lambda2} & B_{1\_\lambda2} & S_{\lambda2} \\ \alpha_{FBS\_\lambda3} & B_{0\_\lambda3} & B_{1\_\lambda3} & S_{\lambda3} \\ \alpha_{FBS\_\lambda4} & B_{0\_\lambda4} & B_{1\_\lambda4} & S_{\lambda4} \end{pmatrix}$$

is known, and $$\begin{pmatrix} C_{FBS} \cdot D \\ \alpha_{PR\_\lambda1} \cdot C_{PR} \cdot D \\ C_{PR} \cdot D \\ A_{offset} \end{pmatrix}$$

is unknown.

In a case where: the wavelength of the second light beam corresponds to the second convergence point; the second light beam is a light beam of 480 nm; the wavelength of the third light beam corresponds to the third convergence point; the third light beam is a light beam of 370 nm; and the fourth light beam is a light beam, a wavelength of the light beam at which the absorbances of both the first material and the second material are converged irrespective of a pH, the pH may be calculated by following expression:

$$\begin{pmatrix} A_{\lambda1} \\ A_{\lambda2} \\ A_{\lambda3} \\ A_{\lambda4} \end{pmatrix} = \begin{pmatrix} \alpha_{FBS\_\lambda1} & 1 & 0 & S_{\lambda1} \\ \alpha_{FBS\_\lambda2} & 0 & B_{1\_\lambda2} & S_{\lambda2} \\ \alpha_{FBS\_\lambda3} & 0 & B_{1\_\lambda3} & S_{\lambda3} \\ 0 & 0 & 0 & S_{\lambda4} \end{pmatrix} \cdot \begin{pmatrix} C_{FBS} \cdot D \\ \alpha_{PR\_\lambda1} \cdot C_{PR} \cdot D \\ C_{PR} \cdot D \\ A_{offset} \end{pmatrix}$$

In the calculating process, a concentration of at least one of the first material and the second material may be calculated based on the expression.

The first material may be fetal bovine serum or bovine calf serum, and the second material may be phenol red.

The first absorption peak may be at or in a vicinity of 410 nm, the second absorption peak may be at or in a vicinity of 430 nm, and the third absorption peak may be at or in a vicinity of 560 nm.

According to the invention, there is also provided a pH measuring apparatus incorporating the pH measuring method.

According to the invention, there is also provided a pH measuring apparatus comprising: a light emitting section configured to emit a plurality of light beams, the plurality of light beams including: a first light beam, a wavelength of which corresponds to a first absorption peak; a second light beam, a wavelength of which corresponds to a second absorption peak or a second convergence point where an absorbance is converged irrespective of a pH; a third light beam, a wavelength of which corresponds to a third absorption peak or a third convergence point where an absorbance is converged irrespective of a pH; and a fourth light beam, a wavelength of the fourth light beam at which an absorbance of at least one of a first material and a second material is converged irrespective of a pH; a light receiving section configured to measure absorbances of the wavelengths of the first to fourth light beams respectively; and a calculating section configured to calculate a pH from values of the absorbances.

DETAILED DESCRIPTION OF EMBODIMENTS

First, relationships between the absorbance and the wavelength of light both in the case where fetal bovine serum (FBS) is contained in a cell culture solution, and in the case where fetal bovine serum (FBS) is not contained in a cell culture solution, or the case of phenol red alone are shown in FIGS. 2 to 6.

Figure 1:
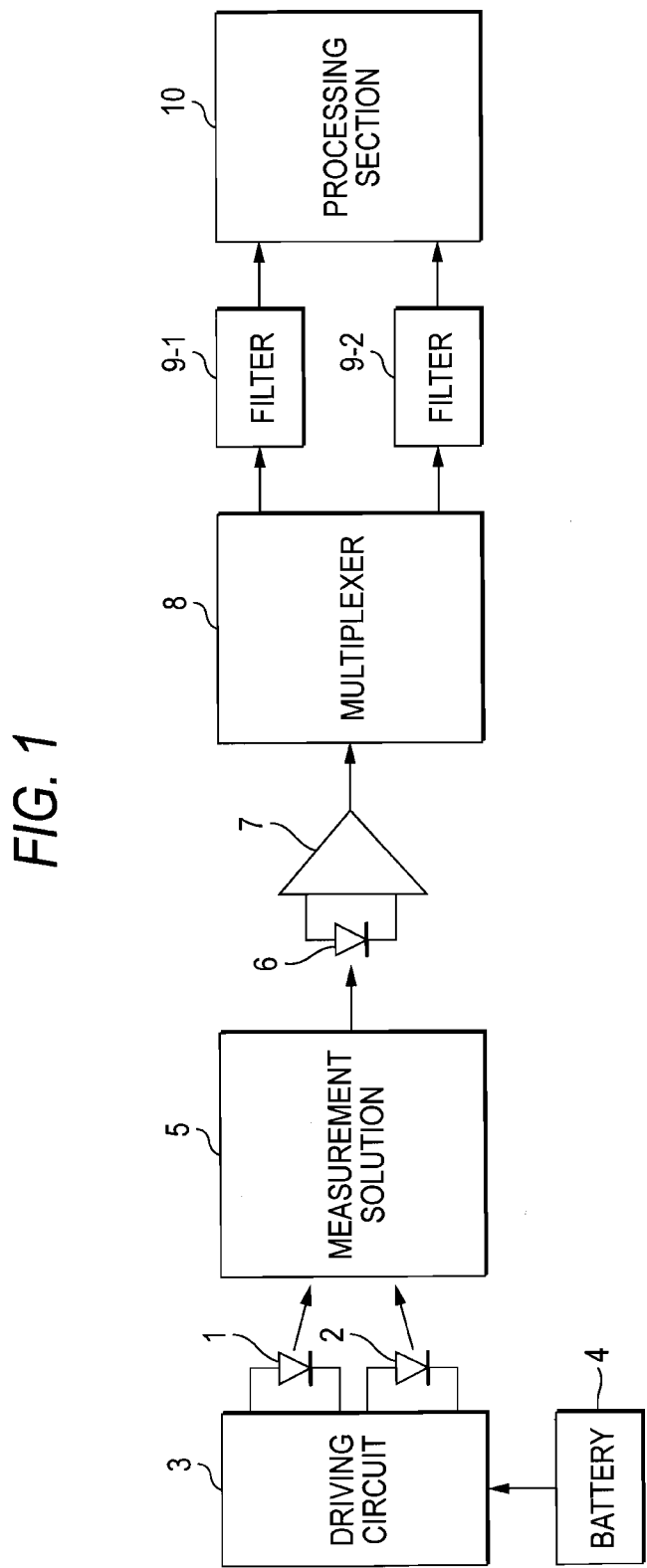
FIG. 1 is a block diagram showing the apparatus for measuring the pH of a solution.
Figure 2:
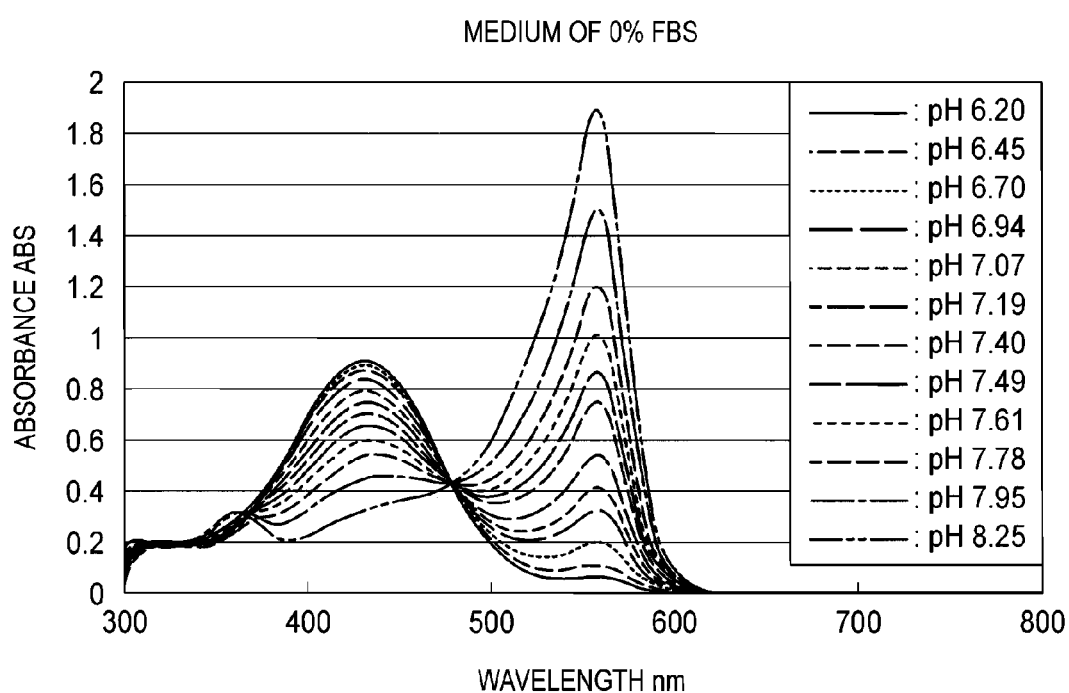
FIG. 2 is a view showing relationships between the absorbance and the wavelength in phenol red alone.

FIG. 2 is a view showing the absorbance of phenol red alone in a usual medium (DMEM) in which fetal bovine serum (FBS) does not exist, at a wavelength of 300 to 800 nm and at pHs of 6.20 to 8.25. In the figure, the abscissa indicates the wavelength in the range of 300 to 800 nm, and the ordinate indicates the absorbance (ABS) in the range of 0 to 2.

In FIG. 2, peaks exist at the wavelengths of 430 nm and 560 nm, and the absorbance is substantially zero at the wavelength of 700 nm. At the wavelengths of 367 nm and 479 nm, the absorbance converges to indicate the same value at all pH values.

Figure 3:
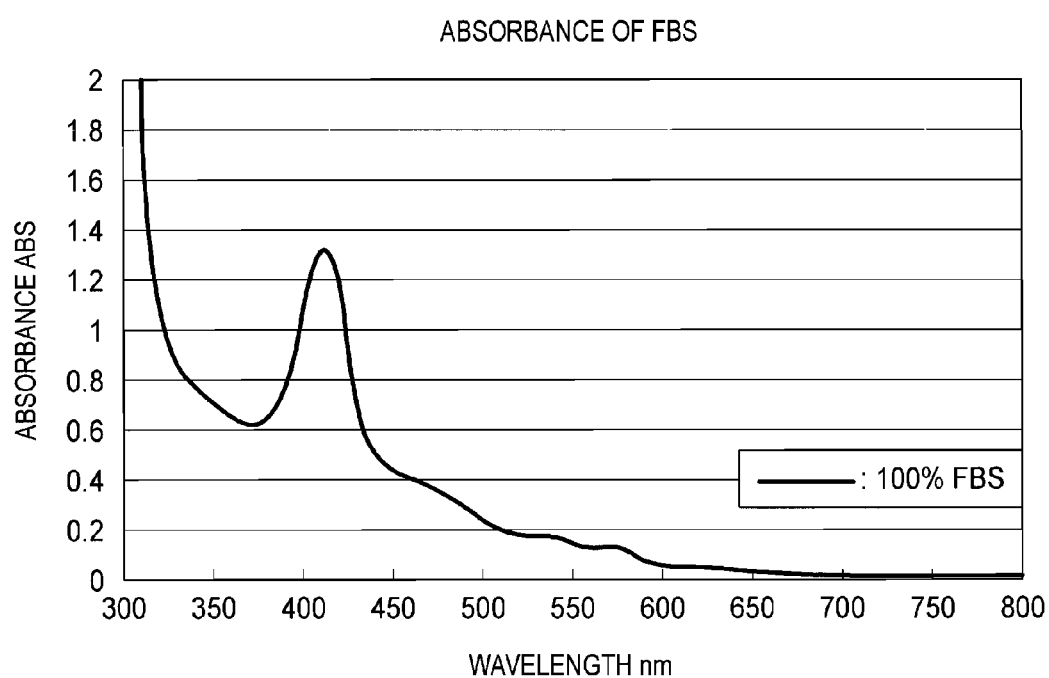
FIG. 3 is a view showing relationships between the absorbance and the wavelength in fetal bovine serum (FBS) alone.

FIG. 3 is a view showing relationships between the absorbance and the wavelength in fetal bovine serum (FBS).

FIG. 3 is a view showing the absorbance in the case of 100% FBS. In the figure, the abscissa indicates the wavelength in the range of 300 to 800 nm, and the ordinate indicates the absorbance (ABS) in the range of 0 to 2.

In FIG. 3, a peak exists in the vicinity of the wavelength of 411 nm, and the absorbance is gradually reduced at the wavelengths other than it.

Figure 4:
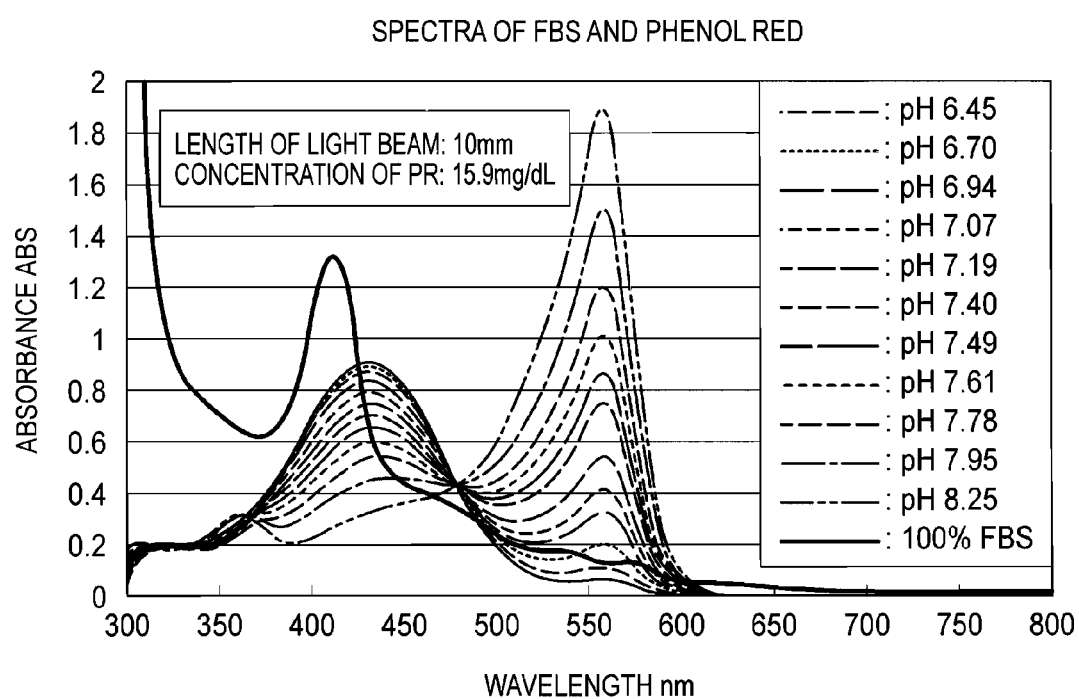
FIG. 4 is a view showing in an overlapping manner the relationships between the absorbance and the wavelength in fetal bovine serum (FBS) alone of FIG. 3, and those in phenol red alone of FIG. 2.

FIG. 4 is a view showing in an overlapping manner the relationships between the absorbance and the wavelength in fetal bovine serum (FBS) of FIG. 3, and those in FIG. 2.

Next, the influence of fetal bovine serum (FBS) exerted on the absorbance of phenol red will be discussed.

FIG. 2 is a view showing relationships between the wavelength and the absorbance of phenol red at 300 to 800 nm in a medium in which fetal bovine serum (FBS) does not exist (0% FBS), at pHs of 6.20 to 8.25.

Figure 5:
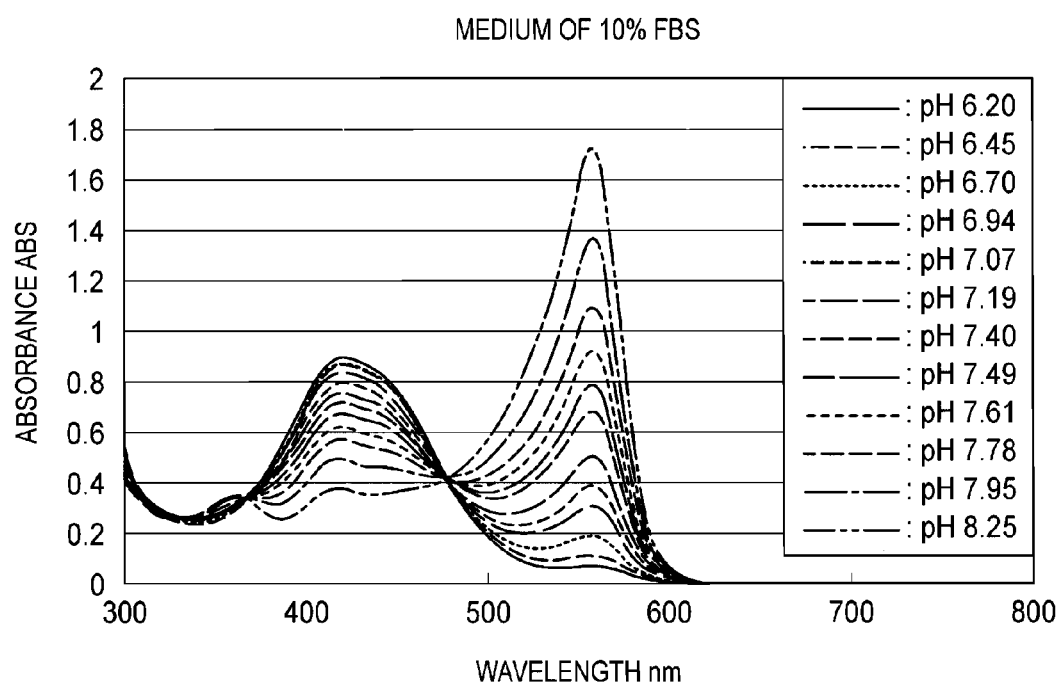
FIG. 5 is a view showing relationships between the wavelength and the absorbance of phenol red at 300 to 800 nm in a medium in which 10% of fetal bovine serum (FBS) exists (10% FBS), at pHs of 6.20 to 8.25.

FIG. 5 is a view showing relationships between the wavelength and the absorbance of phenol red at 300 to 800 nm in a medium in which 10% of fetal bovine serum (FBS) exists (10% FBS), at pHs of 6.20 to 8.25. As compared with FIG. 2, when FBS is mixed, the absorption spectrum of phenol red is changed.

Figure 6:
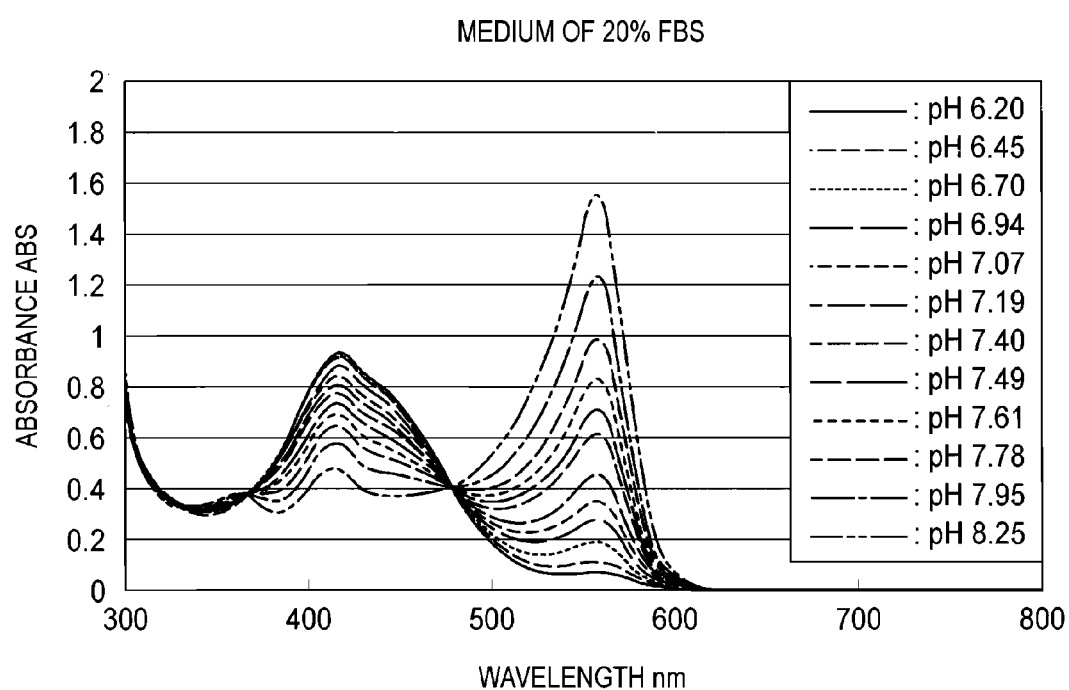
FIG. 6 is a view showing relationships between the wavelength and the absorbance of phenol red at 300 to 800 nm in a medium in which 20% of fetal bovine serum (FBS) exists (20% FBS), at pHs of 6.20 to 8.25.

FIG. 6 is a view showing relationships between the wavelength and the absorbance of phenol red at 300 to 800 nm in a medium in which 20% of fetal bovine serum (FBS) exists (20% FBS), at pHs of 6.20 to 8.25. As compared with FIG. 2, when FBS is further mixed, the absorption spectrum of phenol red is more changed.

As shown in FIGS. 2, 5, and 6, in the case where fetal bovine serum exists in some degree, the premise, which holds in FIG. 2, that, by taking a ratio of absorption in the vicinity of 430 nm to that in the vicinity of 560 nm, the plot shows one curve, and therefore the pH of a culture solution can be calculated from a ratio of two peaks of phenol red is not satisfied. Consequently, it will be seen that the pH value of a cell culture solution cannot be correctly measured.

Figure 7:
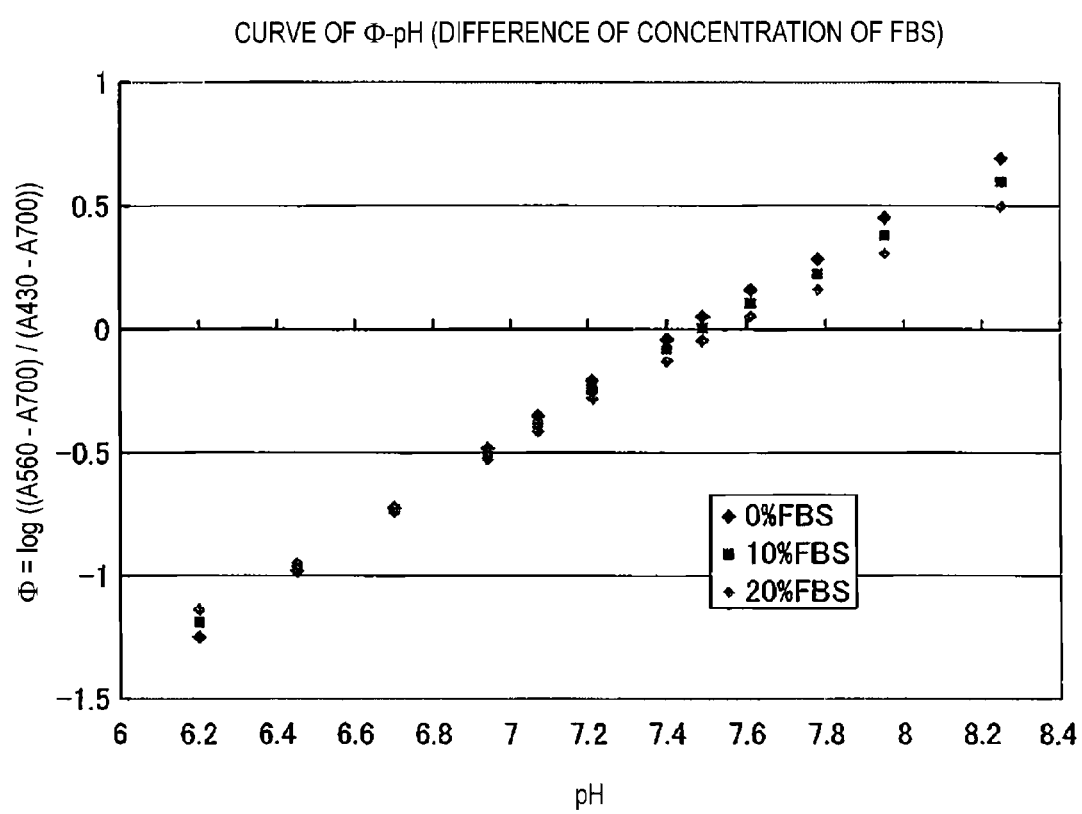
FIG. 7 is a view showing relationships between the logarithm $\Phi$ of the absorbance and the pH due to a difference of the concentration of fetal bovine serum (FBS).

FIG. 7 shows relationships between the logarithm $\Phi$ of the absorbance and the pH.

In FIG. 7, the ordinate indicates the logarithm $\Phi$ of the absorbance, $\Phi = \log((A560-A700)/(A430-A700))$, i.e., a value which is obtained by correcting absorbances at wavelengths of 430 nm and 560 nm by the wavelength of 700 nm, and the abscissa indicates pH 6.20 to pH 8.25. The figure shows medium examples in which fetal bovine serum (FBS) is 0%, 10%, and 20%, respectively.

Figure 8:
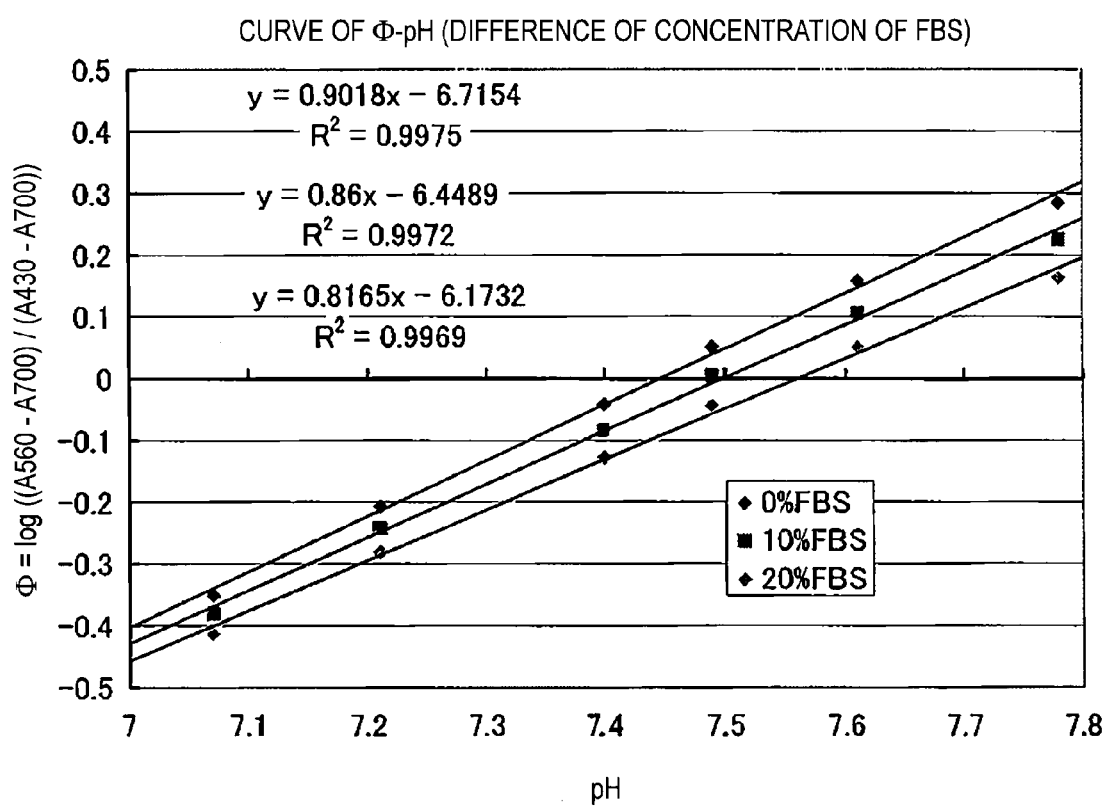
FIG. 8 is a view enlargedly showing a range of pH 7 to pH 7.8 which is a part of the relationships between the logarithm $\Phi$ of the absorbance and the pH shown in FIG. 7.

Next, FIG. 8 shows a range of pH 7 to pH 7.8 which is a part of FIG. 7 showing the relationships between the logarithm $\Phi$ of the absorbance and the pH.

In FIG. 8, the cases where fetal bovine serum (FBS) is 0%, 10%, and 20% can be approximated by the following expressions:

$y1 = 0.9018x - 6.7154$ $R^2 = 0.9975$ (FBS 0%), $y2 = 0.86x - 6.4489$ $R^2 = 0.9972$ (FBS 10%), and $y3 = 0.8165x - 6.1732$ $R^2 = 0.9965$ (FBS 20%).

Next, correction of the influence of fetal bovine serum (FBS) will be described.

In the application, the followings are discussed as a method of correcting the influence of fetal bovine serum (FBS).

As a first correcting method, multiple regression analysis will be described.

For example, the basic expression of multiple regression analysis is expressed by [Expression 1] below. In the expression, B indicates a constant, $\Phi$ indicates the absorbance ratio, and A indicates the absorbance.

$$pH = B_0 + B_1 * \Phi_{\lambda i/\lambda j}$$

$$\Phi_{\lambda i/\lambda j} = \log(A_{\lambda i}/A_{\lambda j})$$

$$pH = B_0 + B_1 * \Phi_{\lambda 1/\lambda 4} + B_2 * \Phi_{\lambda 2/\lambda 4} + B_1 * \Phi_{\lambda 3/\lambda 4} \qquad \text{[Expression 1]}$$

In the regression expression, calculation is performed by using the absorbance at or in a vicinity of 477 nm which is converged in the range where FBS exists at 0% to 20%, to indicate the same value, and the absorbances at 411 nm where FBS alone shows a peak, 430 nm where a first peak of phenol red exists, and 558 nm where a second peak exists.

Figure 9:
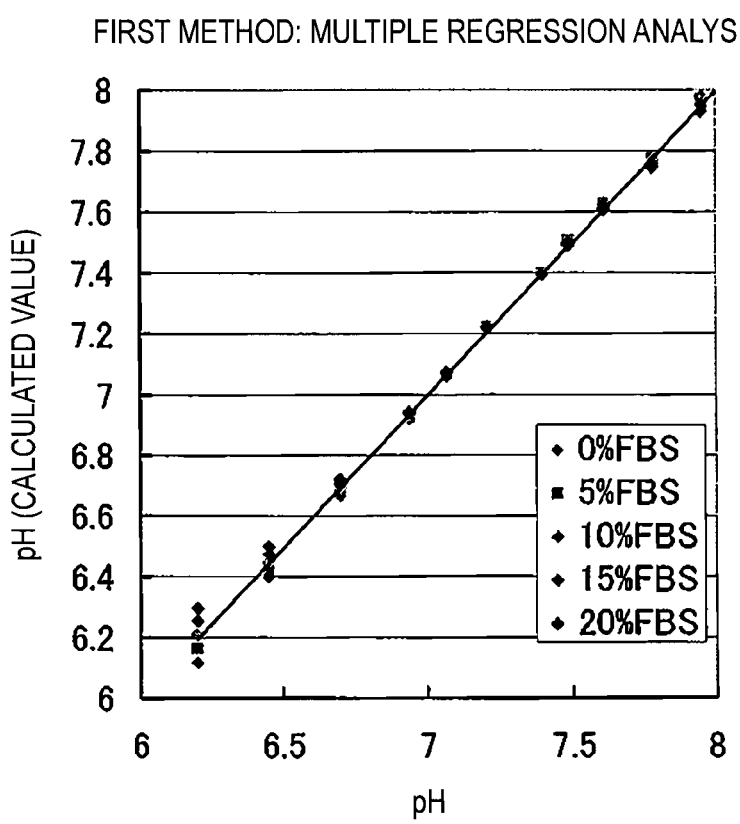
FIG. 9 is a view showing relationships between an actual pH value and a calculated pH value obtained by a regression expression indicated by [Expression 1] due to multiple regression analysis.

FIG. 9 shows relationships between an actual pH value and a calculated pH value obtained by the regression expression indicated by [Expression 1] due to multiple regression analysis.

In the relationships between an actual pH value and a calculated pH value obtained by the regression expression, as shown in FIG. 9, it can be seen that the influence of a change of the concentration of fetal bovine serum (FBS) is large at the pH of 6.5 or less, and small at the pH of 7 or more.

Figure 10:
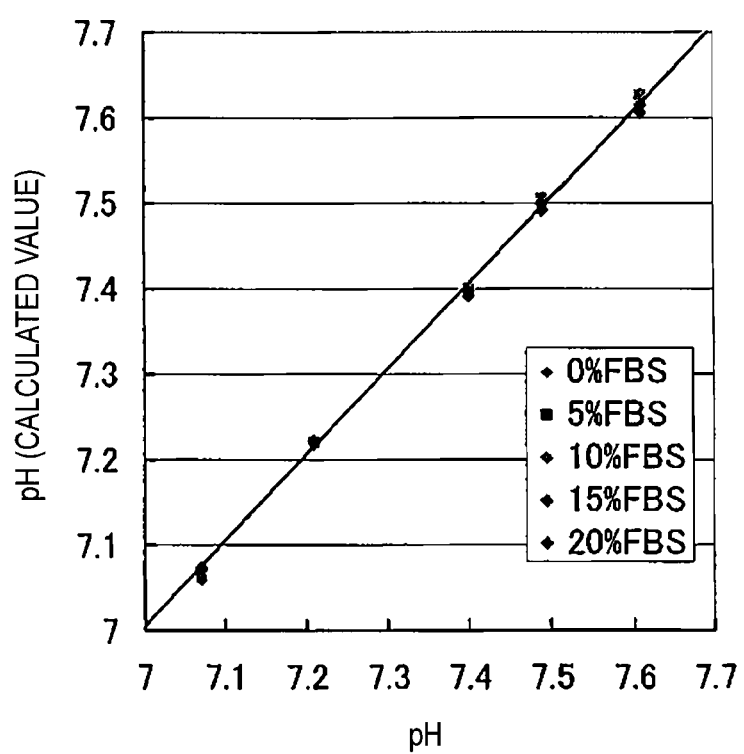
FIG. 10 is a view enlargedly showing a range of pH 7 to pH 7.6 which is a part of the relationships between an actual pH value and a calculated pH value obtained by the regression expression indicated by [Expression 1] due to multiple regression analysis.

FIG. 10 shows an example in a range of pH 7 to pH 7.6.

From the above results, excellent measurements can be performed by multiple regression analysis.

As shown in FIG. 10, in the range of pH 7 to pH 7.6, particularly, the relationships can be approximated by a straight line, and hence more excellent measurements are enabled.

In the above, the example in which a usual medium (DMEM) is used has been described. As a medium, instead of the usual medium (DMEM), SkBM which is specialized in culturing of myoblast cells may be used.

In SkBM, the concentration of phenol red is about 1/10 of that of DMEM. Therefore, the influence of the absorbance of fetal bovine serum (FBS) is largely exerted, and the regression expression which is used in the above multiple regression analysis cannot be applied. In the case where the medium is SkBM, consequently, there remains the problem in that the pH cannot be correctly measured.

As a second correcting method, matrix calculation (simultaneous expression) will be described.

The wavelengths of the light beams emitted from the LEDs in the case where fetal bovine serum (FBS) exists in phenol red are indicated by $\lambda 1$ to $\lambda 4$, respectively. The respective absorbances $A_{\lambda 1}$ to $A_{\lambda 4}$ are indicated by the sum of the absorbance of FBS and that of phenol red as expressed by [Expression 2] below.

$$A_{\lambda 1} = \alpha_{FBS\_\lambda 1} \cdot C_{FBS} \cdot D + \alpha_{PR\_\lambda 1} \cdot C_{PR} \cdot D + A_{offset\_\lambda 1}$$

$$A_{\lambda 2} = \alpha_{FBS\_\lambda 2} \cdot C_{FBS} \cdot D + \alpha_{PR\_\lambda 2} \cdot C_{PR} \cdot D + A_{offset\_\lambda 2}$$

$$A_{\lambda 3} = \alpha_{FBS\_\lambda 3} \cdot C_{FBS} \cdot D + \alpha_{PR\_\lambda 3} \cdot C_{PR} \cdot D + A_{offset\_\lambda 3}$$

$$A_{\lambda 4} = \alpha_{FBS\_\lambda 4} \cdot C_{FBS} \cdot D + \alpha_{PR\_\lambda 4} \cdot C_{PR} \cdot D + A_{offset\_\lambda 4} \qquad \text{[Expression 2]}$$

Figure 11:
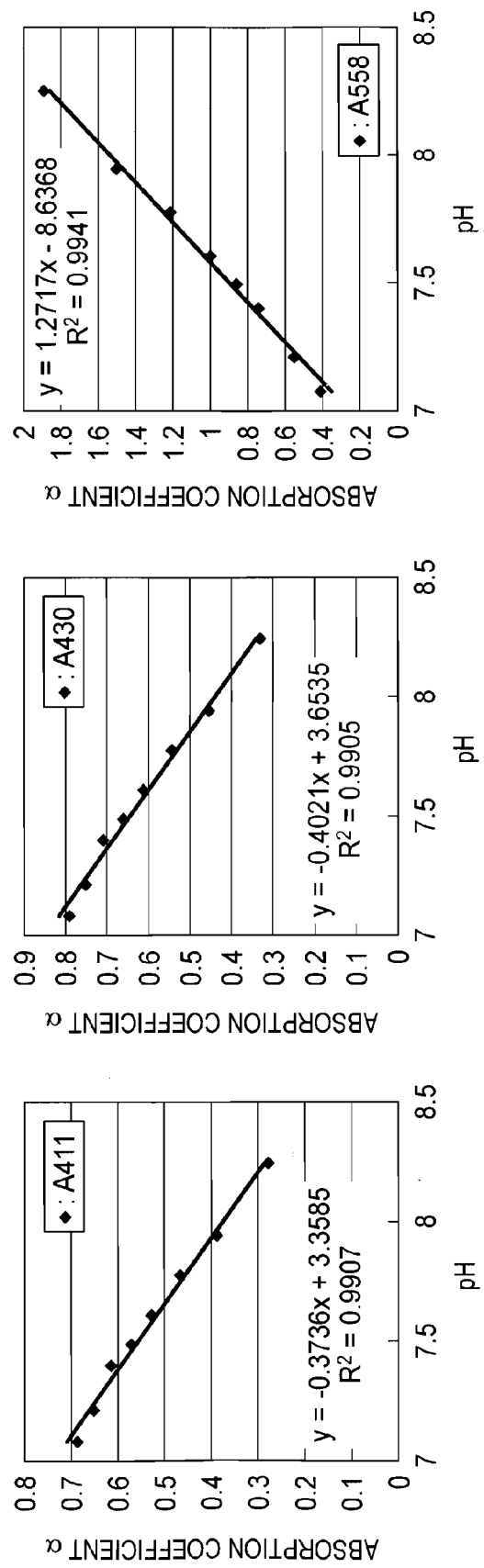
FIG. 11 is a view showing relationships between the absorption coefficient $\alpha_{PR\_J}$ of phenol red and the pH.

As shown in FIG. 11, in the range of pH 7 to pH 8.0, relationships between the absorption coefficient $\alpha_{PR\_\lambda 1}$ of phenol red and the pH can be approximated by a linear expression. In the correcting method, namely, the determinants indicated by [Expression 3] below are constituted as a function in which the pH is an unknown.

[Expression 3]

$$\begin{vmatrix} \alpha_{PR\_\lambda 1} \\ \alpha_{PR\_\lambda 2} \\ \alpha_{PR\_\lambda 3} \\ \alpha_{PR\_\lambda 4} \end{vmatrix} \ldots \text{Linear function of pH}$$

$$\begin{vmatrix} \alpha_{FBS\_\lambda 1} \cdot C_{FBS} \cdot D \\ \alpha_{FBS\_\lambda 2} \cdot C_{FBS} \cdot D \\ \alpha_{FBS\_\lambda 3} \cdot C_{FBS} \cdot D \\ \alpha_{FBS\_\lambda 4} \cdot C_{FBS} \cdot D \end{vmatrix} \ldots \text{First material } (FBS)$$

$$\begin{vmatrix} \alpha_{PR\_\lambda 1} \cdot C_{PR} \cdot D \\ \alpha_{PR\_\lambda 2} \cdot C_{PR} \cdot D \\ \alpha_{PR\_\lambda 3} \cdot C_{PR} \cdot D \\ \alpha_{PR\_\lambda 4} \cdot C_{PR} \cdot D \end{vmatrix} \ldots \text{Second material (pH indicator)}$$

$$\begin{vmatrix} A_{\textit{offset}\_\lambda 1} \\ A_{\textit{offset}\_\lambda 2} \\ A_{\textit{offset}\_\lambda 3} \\ A_{\textit{offset}\_\lambda 4} \end{vmatrix} \ldots \text{Offset (scattering, etc.)}$$

Therefore, the absorbance $A_{\lambda_i}$ can be expressed as [Expression 4] below.

$$A_{\lambda 1} = \alpha_{FBS\_\lambda 1} \cdot C_{FBS} \cdot D + (B_{0\_\lambda 1} \text{pH} + B_{1\_\lambda 1}) \cdot C_{PR} \cdot D + S_{\lambda 1} \cdot A_{\textit{offset}}$$

$$A_{\lambda 2} = \alpha_{FBS\_\lambda 2} \cdot C_{FBS} \cdot D + (B_{0\_\lambda 2} \text{pH} + B_{1\_\lambda 2}) \cdot C_{PR} \cdot D + S_{\lambda 2} \cdot A_{\textit{offset}}$$

$$A_{\lambda 3} = \alpha_{FBS\_\lambda 3} \cdot C_{FBS} \cdot D + (B_{0\_\lambda 3} \text{pH} + B_{1\_\lambda 3}) \cdot C_{PR} \cdot D + S_{\lambda 3} \cdot A_{\textit{offset}}$$

$$A_{\lambda 4} = \alpha_{FBS\_\lambda 4} \cdot C_{FBS} \cdot D + (B_{0\_\lambda 4} \text{pH} + B_{1\_\lambda 4}) \cdot C_{PR} \cdot D + S_{\lambda 4} \cdot A_{\textit{offset}}$$

[Expression 4]

Here, the absorbances at the wavelengths $\lambda 1$ to $\lambda 4$ can be expressed by [Expression 5] below.

[Expression 5]

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ \text{pH} \cdot C_{PR} \cdot D \\ C_{PR} \cdot D \\ A_{\textit{offset}} \end{pmatrix}$$

where $$\begin{pmatrix} A_{\lambda 1} \\ A_{\lambda 2} \\ A_{\lambda 3} \\ A_{\lambda 4} \end{pmatrix}$$

is measurable, $$\begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}$$

is known, and $$\begin{pmatrix} C_{FBS} \cdot D \\ \text{pH} \cdot C_{PR} \cdot D \\ C_{PR} \cdot D \\ A_{\textit{offset}} \end{pmatrix}$$

is unknown.

The pH is obtained from this expression.

According to the calculation of [Expression 1] above, the concentration of FBS, that of phenol red, and the pH can be calculated by substituting the absorbances at the wavelengths (for example, $\lambda 1$ is 411 nm, $\lambda 2$ is 430 nm, $\lambda 3$ is 558 nm, and $\lambda 4$ is 700 nm) in [Expression 6] below.

[Expression 6]

$$\begin{pmatrix} C_{FBS} \cdot D \\ \text{pH} \cdot C_{PR} \cdot D \\ C_{PR} \cdot D \\ A_{\textit{offset}} \end{pmatrix} = \begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}^{-1} \cdot \begin{pmatrix} A_{\lambda 1} \\ A_{\lambda 2} \\ A_{\lambda 3} \\ A_{\lambda 4} \end{pmatrix}$$

Figure 12:
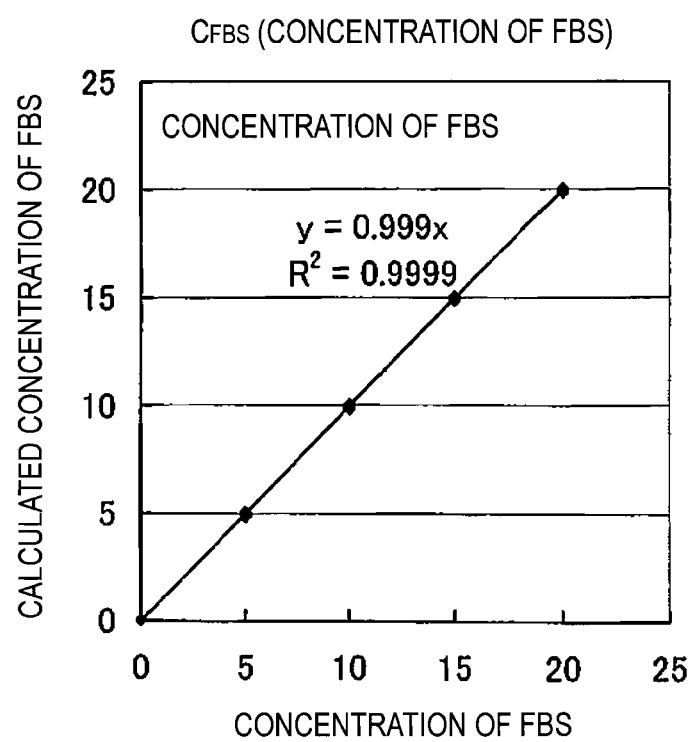
FIG. 12 is a view showing results of calculations by [Expression 5] (relationships between the FBS concentration and a calculated FBS concentration).
Figure 13:
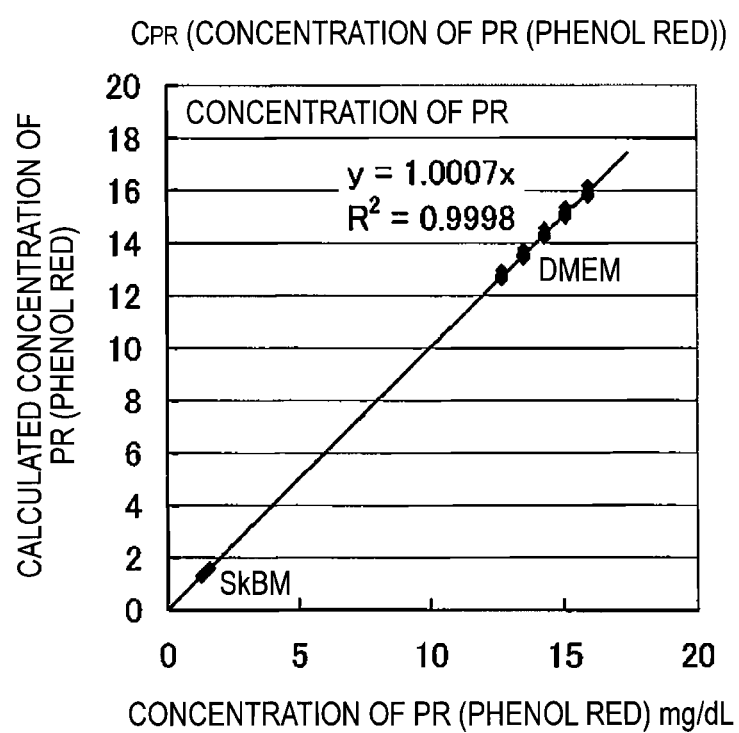
FIG. 13 is a view showing results of calculations by [Expression 5] (relationships between the concentration of phenol red and a calculated concentration of phenol red).
Figure 14:
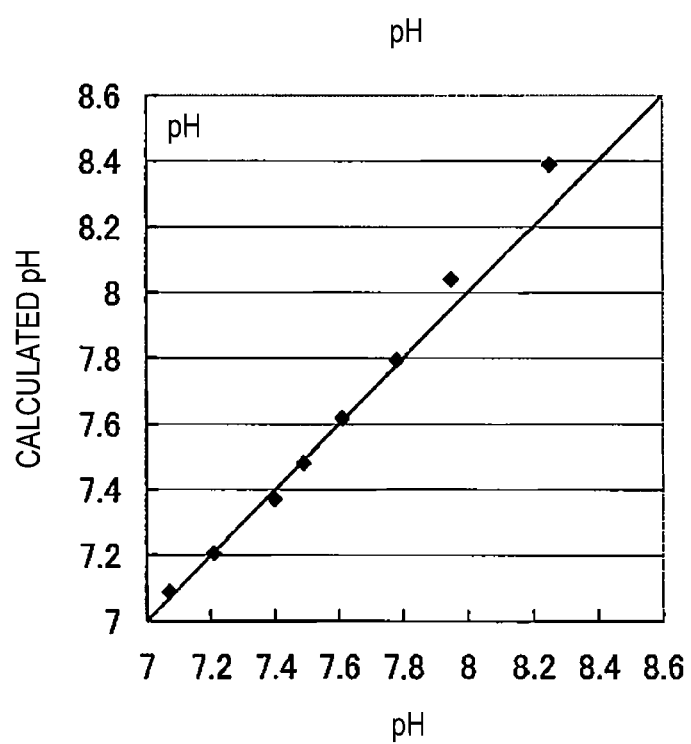
FIG. 14 is a view showing results of calculations by [Expression 5] (relationships between the pH and a calculated pH).

FIGS. 12, 13, and 14 show results of calculations by [Expression 5] above.

As apparent from the calculation results shown in FIGS. 12 to 14, the pH can be calculated irrespective of the concentrations of phenol red and FBS.

As seen from the calculation results shown in FIG. 14, when the pH of the medium is in the range of 7 to 8, the calculation can be performed at an early stage, and monitoring can be continuously conducted. Therefore, this is particularly effective. However, there remains the problem in that a large error is produced outside a predetermined pH range of the medium.

The correction has been described by exemplifying an approximation to a linear function. However, the invention is not limited to this. In the case of an approximation to a quadratic function, a further wavelength may be added, and the calculation may be performed by using a 5×5 determinant.

As a third correcting method, removal of the influence of fetal bovine serum (FBS) will be described.

As described in the second correcting method, when fetal bovine serum (FBS) exists in phenol red, the respective absorbances $A_{\lambda 1}$ to $A_{\lambda 4}$ in the case where the wavelengths of the light beams emitted from the LEDs are indicated by $\lambda 1$ to $\lambda 4$ are indicated by the sum of the absorbance and that of phenol red as expressed by [Expression 7] below.

$$A_{\lambda 1} = \alpha_{FBS\_\lambda 1} \cdot C_{FBS} \cdot D + \alpha_{PR\_\lambda 1} \cdot C_{PR} \cdot D + A_{\textit{offset}\_\lambda 1}$$

$$A_{\lambda 2} = \alpha_{FBS\_\lambda 2} \cdot C_{FBS} \cdot D + \alpha_{PR\_\lambda 2} \cdot C_{PR} \cdot D + A_{\textit{offset}\_\lambda 2}$$

$$A_{\lambda 3}=\alpha_{FBS\_\lambda 3}\cdot C_{FBS}\cdot D+\alpha_{PR\_\lambda 3}\cdot C_{PR}\cdot D+A_{offset\_\lambda 3}$$

$$A_{\lambda 4}=\alpha_{FBS\_\lambda 4}\cdot C_{FBS}\cdot D+\alpha_{PR\_\lambda 4}\cdot C_{PR}\cdot D+A_{offset\_\lambda 4} \quad \text{[Expression 7]}$$

Unlike the second correcting method, the determinants indicated by [Expression 8] below may be constituted as a function in which the absorption coefficient $\alpha_{PR\_\lambda 1}$ is an unknown. [Expression 8] is identical with [Expression 3] above.

[Expression 8]

$$\begin{vmatrix} \alpha_{PR\_\lambda 1} \\ \alpha_{PR\_\lambda 2} \\ \alpha_{PR\_\lambda 3} \\ \alpha_{PR\_\lambda 4} \end{vmatrix} \ldots \text{Linear function of } \alpha_{PR\_\lambda 1}$$

$$\begin{vmatrix} \alpha_{FBS\_\lambda 1}\cdot C_{FBS}\cdot D \\ \alpha_{FBS\_\lambda 2}\cdot C_{FBS}\cdot D \\ \alpha_{FBS\_\lambda 3}\cdot C_{FBS}\cdot D \\ \alpha_{FBS\_\lambda 4}\cdot C_{FBS}\cdot D \end{vmatrix} \ldots \text{First material } (FBS)$$

$$\begin{vmatrix} \alpha_{PR\_\lambda 1}\cdot C_{PR}\cdot D \\ \alpha_{PR\_\lambda 2}\cdot C_{PR}\cdot D \\ \alpha_{PR\_\lambda 3}\cdot C_{PR}\cdot D \\ \alpha_{PR\_\lambda 4}\cdot C_{PR}\cdot D \end{vmatrix} \ldots \text{Second material (pH indicator)}$$

$$\begin{vmatrix} A_{offset\_\lambda 1} \\ A_{offset\_\lambda 2} \\ A_{offset\_\lambda 3} \\ A_{offset\_\lambda 4} \end{vmatrix} \ldots \text{Offset (scattering, etc.)}$$

Therefore, the absorption coefficient $\alpha_{PR\_\lambda 1}$ can be expressed by [Expression 9] below.

$$A_{\lambda 1}=\alpha_{FBS\_\lambda 1}\cdot C_{FBS}\cdot D+\alpha_{PR\_\lambda 1}\cdot C_{PR}\cdot D+S_{\lambda 1}\cdot A_{offset}$$

$$A_{\lambda 2}=\alpha_{FBS\_\lambda 2}\cdot C_{FBS}\cdot D+(B_{0\_\lambda 2}\cdot\alpha_{PR\_\lambda 2}+B_{1\_\lambda 2})\cdot C_{PR}\cdot D+S_{\lambda 2}\cdot A_{offset}$$

$$A_{\lambda 3}=\alpha_{FBS\_\lambda 3}\cdot C_{FBS}\cdot D+(B_{0\_\lambda 3}\cdot\alpha_{PR\_\lambda 3}+B_{1\_\lambda 3})\cdot C_{PR}\cdot D+S_{\lambda 3}\cdot A_{offset}$$

$$A_{\lambda 4}=\alpha_{FBS\_\lambda 4}\cdot C_{FBS}\cdot D+(B_{0\_\lambda 4}\cdot\alpha_{PR\_\lambda 4}+B_{1\_\lambda 4})\cdot C_{PR}\cdot D+S_{\lambda 4}\cdot A_{offset} \quad \text{[Expression 9]}$$

Here, the absorbances at the wavelengths $\lambda 1$ to $\lambda 4$ can be expressed by [Expression 10] below.

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS}\cdot D \\ \alpha_{PR\_\lambda 1}\cdot C_{PR}\cdot D \\ C_{PR}\cdot D \\ A_{offset} \end{pmatrix} \quad \text{[Expression 10]}$$

where $$\begin{pmatrix} A_{\lambda 1} \\ A_{\lambda 2} \\ A_{\lambda 3} \\ A_{\lambda 4} \end{pmatrix}$$

is measurable, $$\begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}$$

is known, and $$\begin{pmatrix} C_{FBS}\cdot D \\ \alpha_{PR\_\lambda 1}\cdot C_{PR}\cdot D \\ C_{PR}\cdot D \\ A_{offset} \end{pmatrix}$$

is unknown.

The pH is obtained by enabling the absorption coefficient at $\lambda 1$ to be calculated.

According to the calculation by [Expression 5] above, $\alpha_{PR\_\lambda 1}$ can be obtained by substituting the absorbances at the wavelengths in [Expression 11] below, and hence the concentration of FBS, that of phenol red, and the pH can be calculated.

Figure 17:
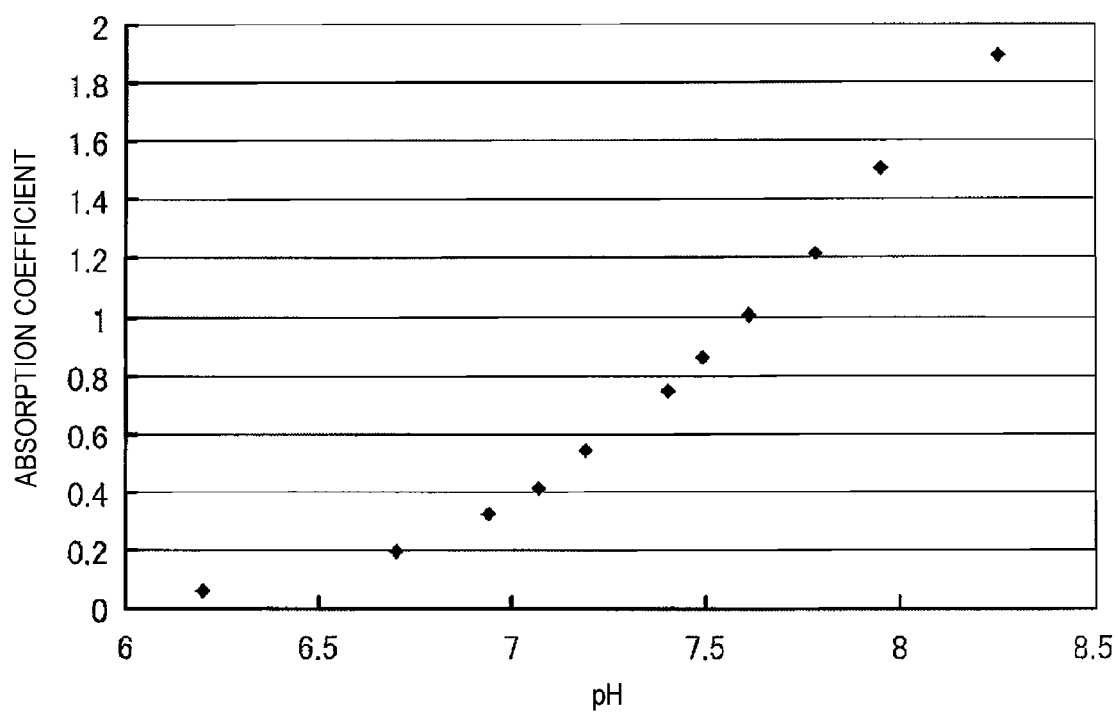
FIG. 17 is a view showing relationships between the absorption coefficient and the pH.

The absorption coefficient and the pH have the relationships shown in FIG. 17. When the absorption coefficient $\alpha_{PR\text{-}\lambda 1}$ is obtained, the pH can be uniquely calculated.

The correction has been described by exemplifying an approximation to a linear function. However, the invention is not limited to this. In the case of an approximation to a quadratic function, a further wavelength may be added, and the calculation may be performed by using a 5×5 determinant.

$$\begin{pmatrix} C_{FBS}\cdot D \\ \alpha_{PR\_\lambda 1}\cdot C_{PR}\cdot D \\ C_{PR}\cdot D \\ A_{offset} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}^{-1} \cdot \begin{pmatrix} A_{\lambda 1} \\ A_{\lambda 2} \\ A_{\lambda 3} \\ A_{\lambda 4} \end{pmatrix} \quad \text{[Expression 11]}$$

As shown in FIG. 2, in the absorbance of phenol red, peaks exist at the wavelengths of 430 nm and 560 nm, and is substantially zero at the wavelength of 700 nm. The wavelengths of 367 nm and 479 nm are wavelengths which may correspond respectively to convergence points where, even when the pH value is changed, absorbances are converged to the same value.

In the case where the characteristics are used and the third correcting method is applied, when, in the calculation of

[Expression 11], the absorbances at the wavelengths (for example, λ1 is 411 nm, λ2 is 478 nm, λ3 is 367 nm, and λ4 is 700 nm) are substituted in [Expression 12] below, elements of the matrix can be replaced with 0. Therefore, the matrix can be simplified, and the concentration of FBS, that of phenol red, and the pH can be accurately calculated.

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ \alpha_{PR\_\lambda 1} \cdot C_{PR} \cdot D \\ C_{PR} \cdot D \\ A_{offset} \end{pmatrix}$$

[Expression 12]

$$\downarrow$$

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & 0 & B_{1\_\lambda 2} & S_{\lambda 2} \\ \alpha_{FBS\_\lambda 3} & 0 & B_{1\_\lambda 3} & S_{\lambda 3} \\ 0 & 0 & 0 & S_{\lambda 4} \end{pmatrix} \cdot \begin{pmatrix} C_{FBS} \cdot D \\ \alpha_{PR\_\lambda 1} \cdot C_{PR} \cdot D \\ C_{PR} \cdot D \\ A_{offset} \end{pmatrix}$$

Figure 15:
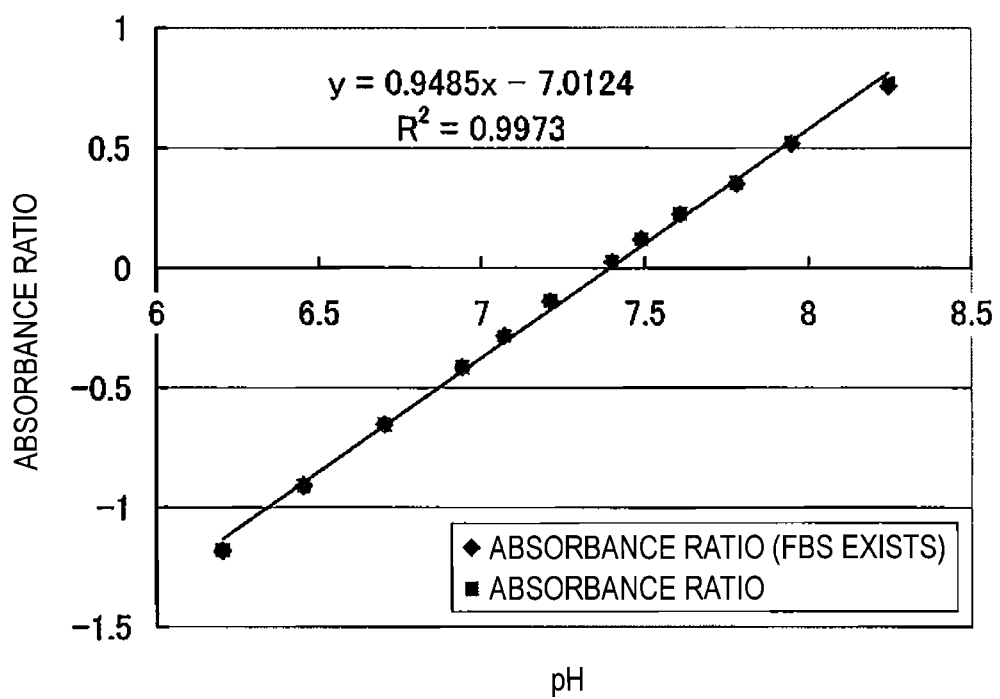
FIG. 15 is a view showing results of calculations by using [Expression 12] in which the abscissa indicates the pH and the ordinate indicates the absorbance ratio.

When results calculated by [Expression 12] are shown in FIG. 15 while the abscissa represents the pH and the ordinate represents the absorbance ratio, it is seen that the results are substantially approximated by a straight line.

Figure 16:
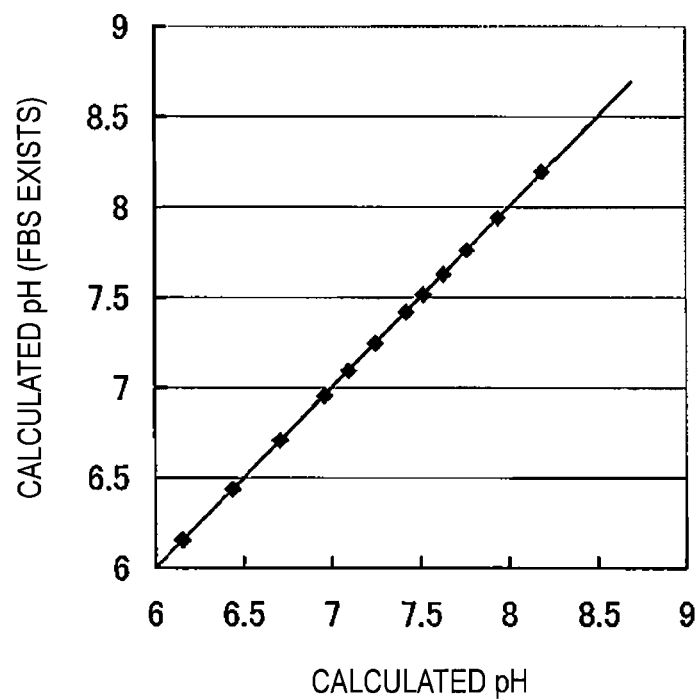
FIG. 16 is a view showing results of calculations by using [Expression 12] (relationships between the pH and a calculated pH).

FIG. 16 shows results of calculations by [Expression 12] (relationships between the pH and a calculated pH).

As seen from FIGS. 15 and 16, the pH can be calculated irrespective of the concentrations of phenol red and FBS, and is well coincident with the pH which is a calculation result of [Expression 4].

The method is particularly effective in that it does not depend on the pH range of the medium, and the stable relationships (linear function) are held.

Phenol red and fetal bovine serum (FBS) which have been exemplified as a pH indicator and a cell proliferation factor in the examples of the invention, respectively. The pH indicator and the cell proliferation factor are not limited to them. In the case where a pH indicator and a cell proliferation factor other than phenol red and fetal bovine serum (FBS) are employed, the values of the wavelengths of the light emitting element may be adequately changed in accordance with their absorption spectra.

According to an aspect of the invention, even in the case where a proliferation factor such as fetal bovine serum (FBS) the concentration of which is unknown is contained in a cell culture solution, the pH value of the cell culture solution can be correctly measured. Even when the concentration of the FBS is momentarily changed, moreover, it is possible to measure the pH value corresponding to the change.

What is claimed is:

1. A pH measuring method comprising:
    illuminating a medium solution with a plurality of light beams,
    the medium solution including:
        a first material which, in a wavelength region of 300 nm to 800 nm, has a first absorption peak; and
        a second material which, in the wavelength region of 300 nm to 800 nm, has a second absorption peak or a second convergence point where an absorbance is converged irrespective of a pH, and a third absorption peak or a third convergence point where an absorbance is converged irrespective of a pH,
    the plurality of light beams including:
        a first light beam, a wavelength of which corresponds to the first absorption peak;
        a second light beam, a wavelength of which corresponds to the second absorption peak or the second convergence point;
        a third light beam, a wavelength of which corresponds to the third absorption peak or the third convergence point; and
        a fourth light beam, a wavelength of the fourth light beam at which an absorbance of at least one of the first material and the second material is converged irrespective of a pH;
    receiving transmitted or reflected light beams of the first to fourth light beams;
    measuring absorbances at the wavelengths of the received transmitted or reflected light beams of the first to fourth light beams respectively; and
    calculating a pH of the medium solution based on the measured absorbances,
    wherein the pH of the medium solution is calculated with an expression including a sum of the absorbance of the first material with the absorbance of the second material.

2. The pH measuring method according to claim 1, wherein the expression includes one of a first function in which the pH is a variable and a second function in which an absorption coefficient is a variable.

3. The pH measuring method according to claim 2, wherein, in a case where the expression includes the first function, the pH is calculated by following expression:

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ pH \cdot C_{PR} \cdot D \\ C_{PR} \cdot D \\ A_{offset} \end{pmatrix}$$

where $$\begin{pmatrix} A_{\lambda 1} \\ A_{\lambda 2} \\ A_{\lambda 3} \\ A_{\lambda 4} \end{pmatrix}$$

is measurable, $$\begin{pmatrix} \alpha_{FBS\_\lambda 1} & B_{0\_\lambda 1} & B_{1\_\lambda 1} & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}$$

is known, and $$\begin{pmatrix} C_{FBS} \cdot D \\ pH \cdot C_{PR} \cdot D \\ C_{PR} \cdot D \\ A_{offset} \end{pmatrix}$$

is unknown.

4. The pH measuring method according to claim 2, wherein, in a case where the expression includes the second function, the pH is calculated based on an absorption coefficient which is obtained by following expression:

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ \alpha_{PR\_\lambda 1} \cdot C_{PR} \cdot D \\ C_{PR} \cdot D \\ A_{offset} \end{pmatrix}$$

where $$\begin{pmatrix} A_{\lambda 1} \\ A_{\lambda 2} \\ A_{\lambda 3} \\ A_{\lambda 4} \end{pmatrix}$$

is measurable, $$\begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}$$

is known, and $$\begin{pmatrix} C_{FBS} \cdot D \\ \alpha_{PR\_\lambda 1} \cdot C_{PR} \cdot D \\ C_{PR} \cdot D \\ A_{offset} \end{pmatrix}$$

is unknown.

5. The pH measuring method according to claim 1, wherein, in a case where:

the wavelength of the second light beam corresponds to the second convergence point;

the second light beam is a light beam of 480 nm;

the wavelength of the third light beam corresponds to the third convergence point;

the third light beam is a light beam of 370 nm; and the fourth light beam is a light beam, a wavelength of the light beam at which the absorbances of both the first material and the second material are converged irrespective of a pH, the pH is calculated by following expression:

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & 0 & B_{1\_\lambda 2} & S_{\lambda 2} \\ \alpha_{FBS\_\lambda 3} & 0 & B_{1\_\lambda 3} & S_{\lambda 3} \\ 0 & 0 & 0 & S_{\lambda 4} \end{pmatrix} \cdot \begin{pmatrix} C_{FBS} \cdot D \\ \alpha_{PR\_\lambda 1} \cdot C_{PR} \cdot D \\ C_{PR} \cdot D \\ A_{offset} \end{pmatrix}.$$

6. The pH measuring method according to claim 1, wherein, in the calculating process, a concentration of at least one of the first material and the second material is calculated based on the expression.

7. The pH measuring method according to claim 1, wherein the first material is fetal bovine serum or bovine calf serum, and the second material is phenol red.

8. The pH measuring method according to claim 1, wherein the first absorption peak is at or in a vicinity of 410 nm, the second absorption peak is at or in a vicinity of 430 nm, and the third absorption peak is at or in a vicinity of 560 nm.

9. A pH measuring apparatus incorporating the pH measuring method according to claim 1.

10. A pH measuring apparatus comprising:
a light emitting section configured to emit a plurality of light beams,
the plurality of light beams including:
a first light beam, a wavelength of which corresponds to a first absorption peak;
a second light beam, a wavelength of which corresponds to a second absorption peak or a second convergence point where an absorbance is converged irrespective of a pH;
a third light beam, a wavelength of which corresponds to a third absorption peak or a third convergence point where an absorbance is converged irrespective of a pH; and
a fourth light beam, a wavelength of the fourth light beam at which an absorbance of at least one of a first material and a second material is converged irrespective of a pH;
a light receiving section configured to measure absorbances of the wavelengths of the first to fourth light beams respectively; and
a calculating section configured to calculate a pH from values of the absorbances,
wherein the pH of the medium solution is calculated with an expression including a sum of the absorbance of the first material with the absorbance of the second material.

11. A pH measuring method comprising:
illuminating a medium solution with a plurality of light beams,
the medium solution including:
a first material which, in a wavelength region of 300 nm to 800 nm, has a first absorption peak; and
a second material which, in the wavelength region of 300 nm to 800 nm, has a second absorption peak or a second convergence point where an absorbance is converged irrespective of a pH, and a third absorption peak or a third convergence point where an absorbance is converged irrespective of a pH,
the plurality of light beams including:
a first light beam, a wavelength of which corresponds to the first absorption peak;
a second light beam, a wavelength of which corresponds to the second absorption peak or the second convergence point;

a third light beam, a wavelength of which corresponds to the third absorption peak or the third convergence point; and a fourth light beam, a wavelength of the fourth light beam at which an absorbance of at least one of the first material and the second material is converged irrespective of a pH;

receiving transmitted or reflected light beams of the first to fourth light beams;

measuring absorbances at the wavelengths of the received transmitted or reflected light beams of the first to fourth light beams respectively; and calculating a pH of the medium solution based on the measured absorbances, wherein the pH of the medium solution is calculated with correction using multiple regression analysis in which a logarithm of an absorbance ratio calculated from the measured absorbances is employed, and wherein the multiple regression analysis is performed by a regression expression indicated by following expression:

$pH = B_0 + B_1 * \Phi_{\lambda y/\lambda j}$ $\Phi_{\lambda i/\lambda j} = \log(A_{\lambda i}/A_{\lambda j})$ $pH = B_0 + B_1 * \Phi_{\lambda 1/\lambda 4} + B_2 * \Phi_{\lambda 2/\lambda 4} + B_1 * \Phi_{\lambda 3/\lambda 4}$.

* * * * *